(12) United States Patent
Yaginuma et al.

(10) Patent No.: US 11,179,217 B2
(45) Date of Patent: Nov. 23, 2021

(54) MEDICAL TREATMENT INSTRUMENT TEMPERATURE INFORMATION MANAGEMENT DEVICE

(71) Applicant: THE YOSHIDA DENTAL MFG. CO., LTD., Tokyo (JP)

(72) Inventors: Tetsuya Yaginuma, Tokyo (JP); Yoshiki Gotani, Tokyo (JP); Takafumi Sato, Tokyo (JP); Keiichi Kudo, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 399 days.

(21) Appl. No.: 16/302,617

(22) PCT Filed: Apr. 21, 2017

(86) PCT No.: PCT/JP2017/016104
§ 371 (c)(1),
(2) Date: Nov. 16, 2018

(87) PCT Pub. No.: WO2017/199689
PCT Pub. Date: Nov. 23, 2017

(65) Prior Publication Data
US 2019/0290383 A1    Sep. 26, 2019

(30) Foreign Application Priority Data

May 18, 2016   (JP) .............................. JP2016-099884

(51) Int. Cl.
*G01N 25/00* (2006.01)
*A61B 90/00* (2016.01)
(Continued)

(52) U.S. Cl.
CPC .............. *A61B 90/06* (2016.02); *A61B 90/90* (2016.02); *A61C 19/00* (2013.01); *A61L 2/04* (2013.01); *A61L 2/26* (2013.01); *A61L 2202/24* (2013.01)

(58) Field of Classification Search
USPC ...................................... 374/120; 340/870.17
See application file for complete search history.

(56) References Cited

U.S. PATENT DOCUMENTS 4,995,402 A *   2/1991   Smith .................... A61B 5/157
                                                        206/569
9,881,250 B2 *   1/2018   Lovell .................... G05B 15/02
(Continued)

FOREIGN PATENT DOCUMENTS

JP        2004-290265        10/2004
JP        2011-060176         3/2011
(Continued)

OTHER PUBLICATIONS

Chu et al. "Study and Simulation of Semi-Active RFID Tags Using Piezoelectric Power Supply for Mobile Process Temperature Sensing" (Year: 2011).*

(Continued)

*Primary Examiner* — Lisa M Caputo
*Assistant Examiner* — Nasir U. Ahmed
(74) *Attorney, Agent, or Firm* — Steven M. Greenberg, Esq.; Shutts & Bowen LLP

(57) ABSTRACT

A medical treatment instrument temperature information management device includes: a wireless tag that is disposed at an instrument; and a reader-writer as a reading unit that reads data from the wireless tag. The wireless tag includes: a temperature sensor; and an IC chip including a storage part. The wireless tag makes the storage part store therein temperature information on temperature of the instrument (Continued)

based on a value detected by the temperature sensor. This makes it possible to manage the temperature information on temperature of the instrument such as a medical treatment instrument with reliability.

17 Claims, 2 Drawing Sheets

(51) Int. Cl.
  *A61B 90/90* (2016.01)
  *A61L 2/04* (2006.01)
  *A61L 2/26* (2006.01)
  *A61C 19/00* (2006.01)

(56) References Cited

U.S. PATENT DOCUMENTS

| | | | | |
|---|---|---|---|---|
| 2006/0140139 | A1* | 6/2006 | DiSilvestro | A61B 5/0028 370/310 |
| 2011/0208170 | A1* | 8/2011 | Hafner | A61B 90/98 606/1 |
| 2011/0292969 | A1 | 12/2011 | Woodard | |
| 2014/0098835 | A1* | 4/2014 | Herzog | G01K 11/265 374/117 |
| 2014/0266695 | A1* | 9/2014 | Addison | A61N 1/3787 340/539.12 |
| 2015/0181840 | A1* | 7/2015 | Tupin, Jr. | A61B 5/0006 600/483 |

FOREIGN PATENT DOCUMENTS

| | | |
|---|---|---|
| JP | 2011-182849 | 9/2011 |
| JP | 2015-142690 | 8/2015 |

OTHER PUBLICATIONS

International Search Report for PCT/JP2017/016104, dated Jun. 6, 2017.
Japanese Office Action for JP2016-099884, dated Jan. 9, 2018.
Japanese Office Action for JP2016-099884, dated Jul. 10, 2018.

* cited by examiner

MEDICAL TREATMENT INSTRUMENT TEMPERATURE INFORMATION MANAGEMENT DEVICE

CROSS-REFERENCE TO RELATED APPLICATIONS

This application is a § 371 national phase entry of International Application No. PCT/JP2017/016104, filed Apr. 21, 2017, which claims priority to Japanese Patent Application No. 2016-099884, filed May 18, 2016.

TECHNICAL FIELD

The present invention relates to a medical treatment instrument temperature information management device which manages temperature information on temperature of a medical treatment instrument.

BACKGROUND ART

A dental instrument such as an air turbine handpiece and a micromotor handpiece, as a medical treatment instrument used in dental therapy, is sterilized in preparation for reuse, after it is used in treatment, procedure, or the like of an affected part such as a tooth in the mouth of a patient.

Regarding sterilization treatment of a dental instrument, Japanese Laid-Open Patent Application, Publication No. 2015-142690 (to be referred to as Patent Document 1 hereinafter) discloses that "Near the sterilization machine 310, the reader/writer (second reading writing means) 311 is provided, and the information currently recorded is read from the wireless tag T with which the hand piece 111 is provided . . . . The management tool 180 records the number of times the reader/writer 311 reads the identification information on the hand piece 111, in the management information storage means 190 for each identification information on the hand piece 111 as the number of times of sterilization of the hand piece 111" (see paragraphs [0063]-[0064]).

RELATED ART DOCUMENT

Patent Document

Patent Document 1: Japanese Laid-Open Patent Application, Publication No.

SUMMARY OF THE INVENTION

Problems to be Solved by the Invention

The technique disclosed in Patent Document 1 fails, however, to recognize that a sterilization treatment in which a medical treatment instrument such as a dental instrument is heated for sterilization has been actually completed. That is, in the technique disclosed in Patent Document 1, completion of a sterilization treatment is recognized when a handpiece (a medical treatment instrument) is brought close to a reader-writer disposed near a sterilizer, which allows the reader-writer to read identification information of the medical treatment instrument from a wireless tag disposed thereat.

This means that the technique disclosed in Patent Document 1 has a possibility that, when the medical treatment instrument is just brought close to the sterilizer, completion of a sterilization treatment is erroneously recognized, even though the sterilization treatment has not yet been actually performed. As described above, there is still room for improvement in management of temperature of a medical treatment instrument concerning a sterilization treatment with heating.

The present invention has been made in light of the background described above and in an attempt to provide a medical treatment instrument temperature information management device which can manage temperature information on temperature of a medical treatment instrument with reliability.

Means for Solving the Problem

A medical treatment instrument temperature information management device which manages temperature information on temperature of a medical treatment instrument includes: a wireless tag that is disposed at the medical treatment instrument and that includes a temperature sensor which detects a temperature of the medical treatment instrument or an ambient temperature thereof, and a storage part; and a reading unit that is configured to read data from the wireless tag. The wireless tag is configured to make the storage part store therein the temperature information, based on a value detected by the temperature sensor.

With the structure described above, the temperature information on temperature of the medical treatment instrument is stored in the storage part of the wireless tag, based on the value detected by the temperature sensor of the wireless tag disposed at the medical treatment instrument. Thus it can be prevented that, for example, even when a sterilization treatment for heating and sterilizing the medical treatment instrument has not yet been actually performed, erroneous information showing that the sterilization treatment has already been performed, though in fact it has not been done, is stored in the storage part of the wireless tag.

The temperature information on temperature of each of the medical treatment instruments can be therefore managed with reliability.

A medical treatment instrument temperature information management device which manages temperature information on temperature of a medical treatment instrument includes: a wireless tag that is disposed at the medical treatment instrument and that includes a temperature sensor which detects a temperature of the medical treatment instrument or an ambient temperature thereof, and a transmission part which is configured to transmit the temperature information, based on a value detected by the temperature sensor; and a storage part that is disposed outside the wireless tag. The wireless tag is configured to transmit the temperature information and make the storage part store therein the transmitted temperature information, based on the value detected by the temperature sensor.

With the structure described above, the temperature information on temperature of the medical treatment instrument is stored in the storage part disposed outside the wireless tag, based on the value detected by the temperature sensor of the wireless tag disposed at the medical treatment instrument. Thus it can be prevented that, for example, even when a sterilization treatment for heating and sterilizing the medical treatment instrument has not yet been actually performed, erroneous information showing that the sterilization treatment has already been performed is stored in the externally-provided storage part.

The temperature information on temperature of each of the medical treatment instruments can be therefore managed with reliability.

In the medical treatment instrument temperature information management device, the wireless tag is preferably but not necessarily configured to make the storage part store therein the temperature information, when the value detected by the temperature sensor reaches a prescribed temperature range.

With the structure described above, when the value detected by the temperature sensor has reached the prescribed temperature range, the storage part of the wireless tag disposed at the medical treatment instrument can store therein such necessary temperature information. Thus it can be prevented that, even when the detected value has not yet reached the prescribed temperature range, erroneous information on the temperature is stored in the storage part.

In the medical treatment instrument temperature information management device, the prescribed temperature range is preferably but not necessarily a temperature range equal to or higher than a sterilization temperature in a sterilization treatment to the medical treatment instrument.

With the structure described above, when a sterilization treatment in which the medical treatment instrument is heated for sterilization, such necessary temperature information can be stored in the storage part of the wireless tag disposed at the medical treatment instrument. Thus it can be prevented that, even when the sterilization treatment has not yet been actually performed to the medical treatment instrument, erroneous information indicating that the sterilization treatment has already been performed is stored in the storage part of the wireless tag at the medical treatment instrument. This makes it possible to prevent that the medical treatment instrument to which necessary sterilization treatment has not yet been subjected is improperly used.

In addition, in this embodiment, when the temperature sensor detects that the medical treatment instrument has reached a temperature range equal to or higher than a sterilization temperature, information indicating that the sterilization treatment has already been performed is automatically stored in the storage part of the wireless tag. Therefore, unlike in the conventional technology, there is no need for a user such as a doctor of a dental clinic or the like to take the trouble of bringing the medical treatment instrument close to the reader-writer so as to make the reader-writer read the wireless tag before and after the sterilization treatment. Failure in storing necessary temperature information in the storage part of the wireless tag can also be prevented.

In the medical treatment instrument temperature information management device, the temperature information preferably but not necessarily includes sterilization information indicating the number of times of sterilization which is the number of times sterilization treatments have been performed to the medical treatment instrument.

With the structure described above, it is possible to know, whenever necessary, the number of times of sterilization having been performed to the medical treatment instrument. Thus, how much number of times sterilization has been performed to each of the medical treatment instruments can be checked. Maintenance of each of the medical treatment instruments can also be managed.

In the medical treatment instrument temperature information management device, the temperature information preferably but not necessarily includes another sterilization information indicating a sterilization date and time which is a date and time when a sterilization treatment has been performed to the medical treatment instrument.

With the structure described above, it is possible to know, whenever necessary, the date and time when the sterilization has been performed to the medical treatment instrument. The latest date and time of the sterilization of the medical treatment instrument can be thereby checked. Maintenance of each of the medical treatment instruments can also be managed.

In the medical treatment instrument temperature information management device, the prescribed temperature range is preferably but not necessarily a temperature range within which a temperature is not suitable for storing the medical treatment instrument.

With the structure described above, when the medical treatment instrument has a temperature within a range too high or too low to be stored in good condition within which a temperature of a surrounding environment of the medical treatment instrument during transportation after shipment or during storage is not appropriate, the storage part of the wireless tag can store therein information indicating that the temperature is not suitable for storing the medical treatment instrument. Similarly, when, for example, a motor or any other component of the medical treatment instrument generates abnormal heat, the storage part of the wireless tag stores therein such temperature information. Thus, when performance of the medical treatment instrument is decreased or a periodic maintenance thereof is carried out, for example, a manufacture reads the temperature information stored in the storage part of the wireless tag and can make use of the information for finding cause of a failure or the like. This makes it possible to smoothly fix or maintain the medical treatment instrument.

In the medical treatment instrument temperature information management device, the value detected by the temperature sensor is preferably but not necessarily stored successively in the storage part.

With the structure described above, a temperature history along with passage of time of each of the medical treatment instruments can be managed.

In the medical treatment instrument temperature information management device, the wireless tag preferably but not necessarily has a battery built therein.

With the structure described above, the wireless tag can obtain a value detected by the temperature sensor any time when necessary, with power supplied by the battery. Therefore, wherever the medical treatment instrument is placed, the wireless tag can make the storage part store therein temperature information on temperature of the medical treatment instrument.

The medical treatment instrument temperature information management device preferably but not necessarily further includes a wireless power feeder which supplies power to the wireless tag without contact thereto.

With the structure described above, the wireless tag can obtain a value detected by the temperature sensor through power supply from the wireless power feeder. This makes it possible for the wireless tag to have a simple and compact structure. This also allows the wireless tag to make the storage part store therein temperature information on temperature of the medical treatment instrument as long as the wireless tag can receive power from the wireless power feeder.

In the medical treatment instrument temperature information management device, the medical treatment instrument is preferably but not necessarily a dental instrument.

With the structure described above, temperature information on temperature of each of the medical treatment instruments can be managed with reliability.

In medical treatment instrument temperature information management device, at least an antenna of the reading unit is preferably but not necessarily disposed on a hanger of the dental treatment apparatus. The hanger is used for holding the dental instrument.

With the structure described above, the medical treatment instrument is held in the hanger of the dental treatment apparatus when the medical treatment instrument is used for dental treatment. This allows that the reading unit in which at least the antenna is disposed on the hanger can read the wireless tag disposed at the medical treatment instrument. A user such as a doctor of a dental clinic or the like can thereby know temperature information on temperature of the medical treatment instrument. Thus, for example, erroneous usage of a medical treatment instrument which has not yet been subjected to necessary sterilization treatment can be further prevented.

In the medical treatment instrument temperature information management device, the reading unit is preferably but not necessarily connected to a communication network and is configured to communicate the temperature information with an information processor connected to the communication network.

With the structure described above, the temperature information on temperature of the medical treatment instrument can be checked at the information processor on the communication network. Also, the temperature information on temperature of the medical treatment instrument can be stored in the information processor. Thus, various types of information on maintenance, failure, advice, or the like regarding the medical treatment instrument can be obtained from the information processor.

Advantageous Effect of the Invention

The present invention can provide a medical treatment instrument temperature information management device which can manage temperature information on temperature of a medical treatment instrument with reliability.

EMBODIMENTS FOR CARRYING OUT THE INVENTION

Figure 1:
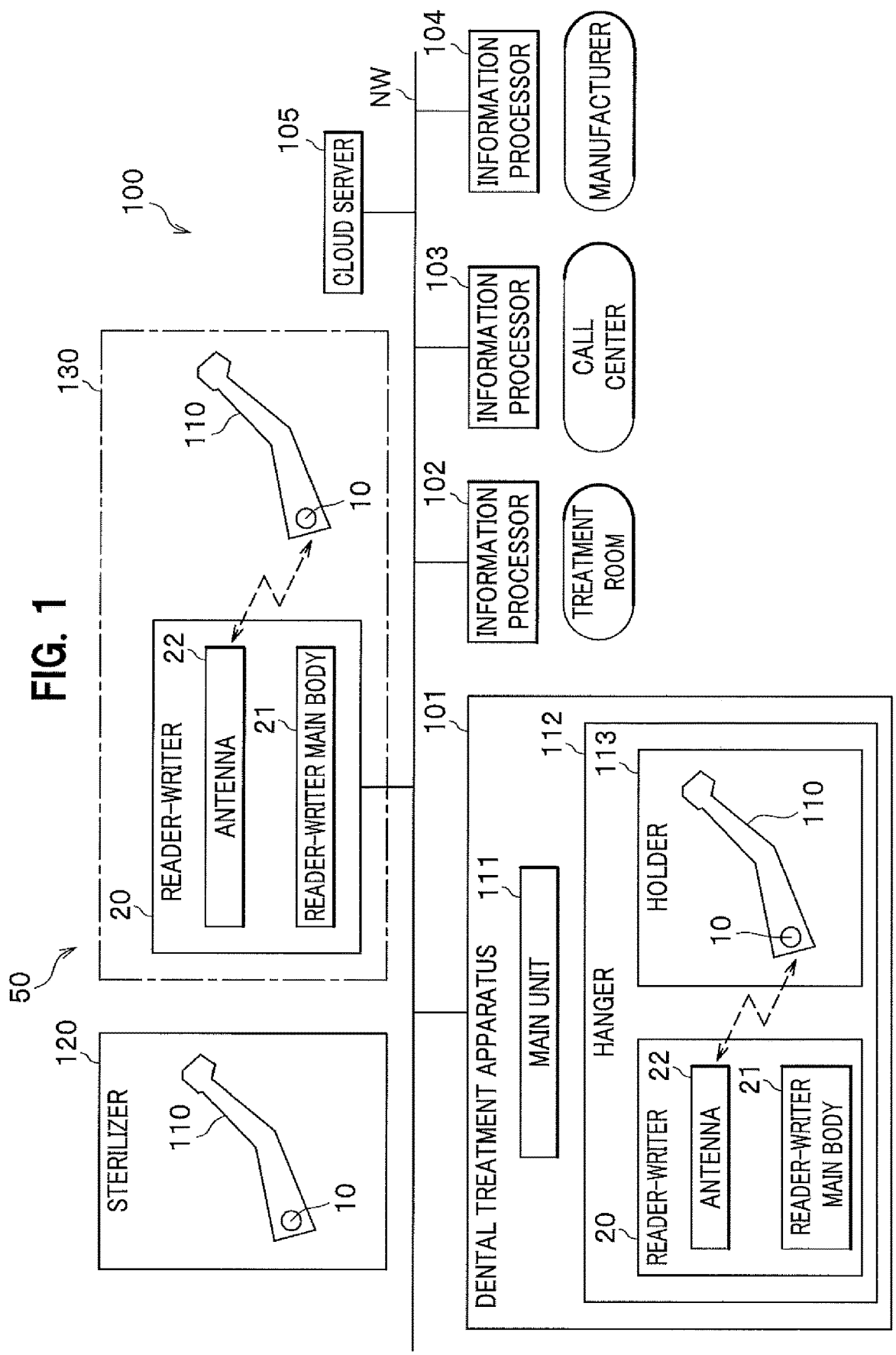
FIG. 1 is a block diagram schematically illustrating a dental treatment service system to which a dental treatment instrument temperature information management device is applied, according to an embodiment of the present invention.

Embodiments of the present invention are described in detail with reference to related drawings.

In the drawings, the same reference numerals are given to components common to or similar to those in different drawings, and duplicate description thereof is omitted herefrom where appropriate.

FIG. 1 is a block diagram schematically illustrating a dental treatment service system 100 to which a medical treatment instrument temperature information management device 50 is applied, according to an embodiment of the present invention.

As illustrated in FIG. 1, the dental treatment service system 100 includes at least one unit of a dental treatment apparatus 101 which is installed in a treatment room of a dental clinic. The dental treatment service system 100 also includes a sterilizer 120 which performs a sterilization treatment by heating, to a dental instrument (which may also be simply referred to as an "instrument" hereinafter) 110 as a medical treatment instrument.

The dental treatment apparatus 101 is an apparatus used when dental treatment is provided to a patient, and includes, as major components thereof: a main unit 111; a hanger 112 disposed on the main unit 111; a table (not shown) on the main unit 111; and a patient chair (not shown).

The hanger 112 of the dental treatment apparatus 101 includes a plurality of holders 113, each of which holds one unit of the respective instruments 110 (in FIG. 1, only one of the holders 113 is illustrated).

An air turbine handpiece, a micromotor handpiece, or the like is used as the instrument 110, for example. The air turbine handpiece grinds a tooth by rotating a burr powered by compressed air at high speed, while spraying water. The micromotor handpiece grinds a tooth by rotating a burr powered by an electric motor at high speed, while spraying water. Any other type of instruments may also be used such as an airmatic handpiece driven by an air motor and a scaler.

A commonly known sterilizer such as, for example, an autoclave using high temperature and high pressure steam can be used as the sterilizer 120. The sterilizer 120 is installed in a treatment room or any other room.

The medical treatment instrument temperature information management device 50 according to this embodiment is a device for managing temperature information on temperature of the instrument 110. The medical treatment instrument temperature information management device 50 includes: a wireless tag 10 disposed at the instrument 110; and a reader-writer 20 which performs communications with the wireless tag 10. The reader-writer 20 has a function of reading data from the wireless tag 10 as a reading unit, and a function of writing data thereinto as a writing unit.

The wireless tag 10 is disposed on, for example, a side nearer to a base end (that is, a side nearer to a joint with a hose) of an outer surface of the instrument 110. At minimum, information for identifying the instrument 110 is previously written into a storage part 11b (see FIG. 2) of the wireless tag 10. The information on identification of the instrument 110 includes a type of the instrument 110 (for example, information indicating that the instrument 110 is an air turbine handpiece).

Figure 2:
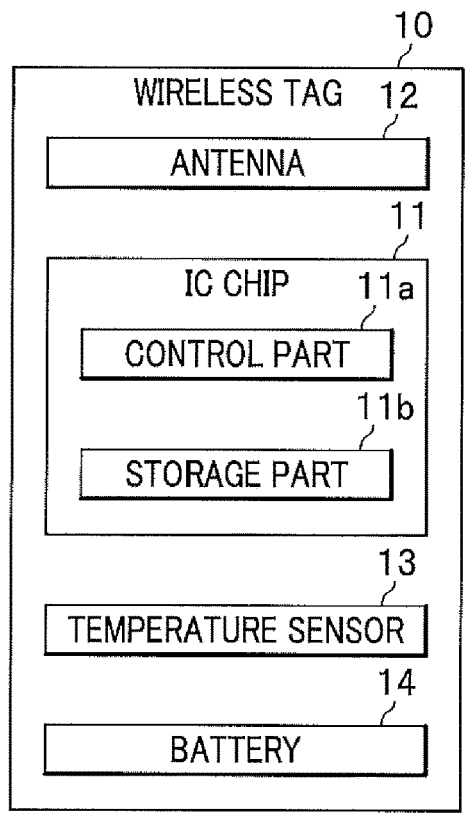
FIG. 2 is a diagram schematically illustrating a structure of a wireless tag according to the embodiment.

FIG. 2 is a diagram schematically illustrating a structure of the wireless tag 10.

The wireless tag 10 is a non-contact electronic tag using wireless communication. An RFID tag, for example, can be used as the wireless tag 10.

As illustrated in FIG. 2, the wireless tag 10 includes: an IC chip 11; and an antenna 12 connected to the IC chip 11. The IC chip 11 includes: a control part 11a which totally controls the wireless tag 10; and the storage part 11b which stores therein various types of information. The control part 11a used herein is composed of a CPU. Alternatively, the control part 11a may be a control circuit constituted by hardware. The antenna 12 is composed of a coil.

The wireless tag 10 includes a temperature sensor 13 and a battery 14. The temperature sensor 13 detects a temperature of the instrument 110 or an ambient temperature of the instrument 110. The temperature sensor 13 can detect a temperature equal to or higher than a sterilization temperature in a sterilization treatment performed by the sterilizer 120 (for example, 150 degrees C.). The wireless tag 10 as a whole is made to have heat resistance of about, for example, 150 to 200 degrees C. The battery 14 used herein has a sealing structure with high heat resistance.

As illustrated in FIG. 1, the reader-writer 20 includes: a reader-writer main body 21 which includes a control part (not shown); and an antenna 22 which is connected to the reader-writer main body 21.

The reader-writer 20 is disposed in the hanger 112 for holding the instrument 110, of the dental treatment apparatus 101. Herein, one unit of the reader-writer 20 which can respond to each of a plurality of the wireless tags 10 disposed at the respective instruments 110 is disposed in the hanger 112. In this case, the reader-writer 20 and the wireless tag 10 preferably have an appropriate relatively-large communication distance therebetween. Alternatively, the reader-writer 20 may be disposed in each of a plurality of the holders 113. In this case, the reader-writer 20 and the wireless tag 10 preferably have an appropriate relatively-small communication distance therebetween.

Another structure of the reader-writer 20 is also possible in which the antenna 22 is disposed on the hanger 112 or the holder 113, and the reader-writer main body 21 is disposed at the main unit 111, a table on the main unit 111, or the like, other than the hanger 112.

FIG. 1 illustrates an example in which another unit of the reader-writer 20 is disposed at the instrument 110 in a container 130. That is, the reader-writer 20 is set inside the container 130. The reader-writer 20 may be, however, set outside the container 130. Or, another structure is also possible in which the antenna 22 of the reader-writer 20 is disposed inside the container 130 and the reader-writer main body 21 thereof is disposed outside and adjacent to the container 130.

Where to dispose the reader-writer 20 is not specifically limited. The reader-writer 20 may be disposed on, for example, a desk of a user such as a doctor in a treatment room or may be attached to the sterilizer 120.

When the wireless tag 10 receives electromagnetic waves radiated from the reader-writer 20, action of electromagnetic induction causes electric current to flow in the wireless tag 10. This allows the wireless tag 10 to perform wireless communication with the reader-writer 20 and read and/or write (which may also be referred to as "read/write" hereinafter) various types of information on the instrument 110.

The reader-writer 20 can read/write various types of information including, for example, usage information such as a use history of the instrument 110 and lubrication information such as a lubrication history of the instrument 110, from/into the wireless tag 10.

In this embodiment, the reader-writer 20 can read temperature information which is information on temperature of the instrument 110, from the wireless tag 10.

When a value detected by the temperature sensor 13 reaches a prescribed temperature range, the wireless tag 10 is configured to make the storage part 11b store therein temperature information on temperature of the instrument 110.

One example of the prescribed temperature range is a temperature range equal to or higher than a sterilization temperature in a sterilization treatment performed to the instrument 110 (for example, 134 degrees C.). In this case, the temperature information stored in the storage part 11b is information showing that the sterilization treatment has been performed to the instrument 110. Specifically, the temperature information includes sterilization information indicating the number of times sterilization treatments are performed to the instrument 110. The temperature information preferably includes another sterilization information indicating a date and time when a sterilization treatment has been performed to the instrument 110. The temperature information preferably includes still another sterilization information indicating a period of time during which a sterilization treatment has been performed to the instrument 110.

Another example of the prescribed temperature range is a temperature range in which a temperature is too low or too high to store the instrument 110 in good condition. In this case, the temperature information stored in the storage part 11b includes information on storage within a temperature range within which a temperature is not suitable for storing the instrument 110, such as: a value detected by the temperature sensor 13; a date and time at which the value was detected; and a period of time during which the instrument 110 was exposed to a temperature within the temperature range.

In this embodiment, both a temperature range in which a temperature is equal to or higher than a sterilization temperature in a sterilization treatment performed to the instrument 110 and a temperature range in which a temperature is too low or too high to store the instrument 110 in good condition are set as the prescribed temperature ranges.

As illustrated in FIG. 1, the reader-writer 20 is connected to the communication network NW. The communication network NW is a wired communication network such as a wired LAN, a wireless communication network such as a wireless LAN and Bluetooth (registered trademark), the Internet, or the like.

The dental treatment apparatus 101 and the information processor 102 installed in a treatment room of a dental clinic described above are connected to the communication network NW. The information processor 103 installed at a call center at which requests for repair and maintenance of the instrument 110 are received, and the information processor 104 set up at a manufacturer which manufactures the instrument 110 are also connected to the communication network NW. Each of those information processors 102 to 104 is, for example, a generally-available personal computer (PC), a mobile terminal such as a tablet PC, or the like. The cloud server 105 is also connected to the communication network NW.

The reader-writer 20 can communicate various types of information such as the lubrication information, with the dental treatment apparatus 101, the information processors 102 to 104, and the cloud server 105, each of which is connected to the communication network NW.

Operations of the medical treatment instrument temperature information management device 50 in the dental treatment service system 100 having the structure as described above are explained with reference to FIG. 3.

Figure 3:
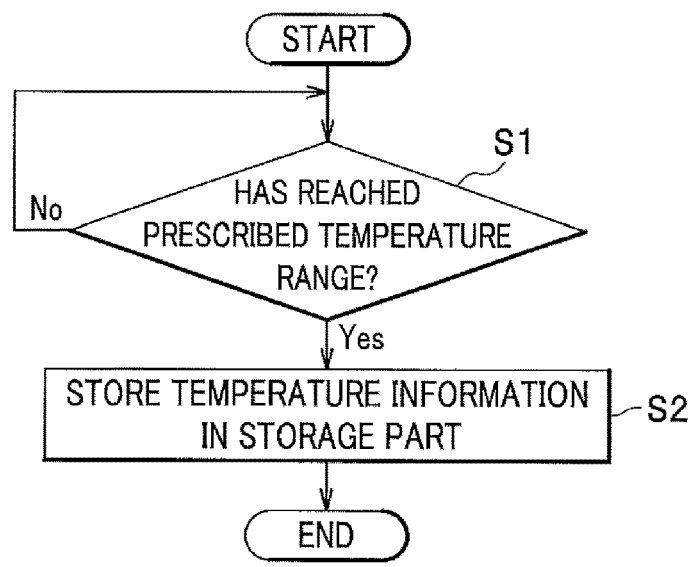
FIG. 3 is a flowchart illustrating outlined steps of a processing of managing temperature information on temperature of an instrument according to the embodiment.

FIG. 3 is a flowchart illustrating outlined steps of a processing of managing temperature information on temperature of the instrument 110.

As illustrated in FIG. 3, in step S1, it is determined whether or not a temperature of the instrument 110 has reached a prescribed temperature range. That is, the wireless tag 10 determines whether or not a value detected by the temperature sensor 13 has reached the prescribed temperature range.

If the temperature of the instrument 110 is not determined to have reached the prescribed temperature range in step S1 (if No in step S1), the processing stands by as it is. If the temperature of the instrument 110 is determined to have reached the prescribed temperature range in step S1 (if Yes in step S1), the processing advances to step S2.

In step S2, the wireless tag 10 makes the storage part 11b store therein the temperature information on temperature of the instrument 110.

More specifically, in this embodiment, if a value detected by the temperature sensor 13 becomes equal to or higher than a sterilization temperature in a sterilization treatment to the instrument 110, the wireless tag 10 makes the storage part 11b store therein the sterilization information described above, as the temperature information.

In this embodiment, if a temperature value detected by the temperature sensor 13 has reached a temperature range in which the temperature of interest is too low or too high to store the instrument 110 in good condition, the wireless tag 10 makes the storage part 11b store therein the storage information described above, as the temperature information.

The various types of information such as the temperature information stored in the storage part 11b of the wireless tag 10 is read by the reader-writer 20 disposed at the hanger 112, when, for example, the instrument 110 equipped with the wireless tag 10 is held in the hanger 112 of the dental treatment apparatus 101. The temperature information herein is the sterilization information or the storage information of each of the instruments 110 and includes identification information for identifying the each of the instruments 110. The information read by the reader-writer 20 is transmitted to the dental treatment apparatus 101, the information processors 102 to 104, and the cloud server 105, via the communication network NW. The information is then displayed in a display of any of those apparatuses or is stored in a storage part thereof.

A user such as a doctor of a dental clinic can thus make the temperature information on temperature of the instrument 110 display in a display of the dental treatment apparatus 101 or the information processor 102, and check up on the information. The temperature information on temperature of the instrument 110 can also be displayed and checked in the information processor 103 installed in a call center or the information processor 104 set up in a manufacturer.

Such a manufacturer can, for example, check up on temperature of the instrument 110 displayed in a dental clinic, using the information processor 104, or can make the information processor 102 installed in the dental clinic display an announcement, via the information processor 104. The announcement herein includes, for example: information such as information on repair and maintenance, how to perform an appropriate sterilization treatment, and information on component replacement; and notification such as "Please contact our salesperson". Knowing in advance the temperature information of the instrument 110 installed in the dental clinic makes it possible to send a serviceperson of a manufacturer or the like to the dental clinic for adjusting or replacing components before a failure occurs. In such a case, the serviceperson can prepare necessary equipment for exchange or the like before his/her visit, based on the previously-obtained information.

A call center can receive a phone call from a user such as a doctor of a dental clinic or the like, when a failure occurs in the instrument 110 of the user. The user such as a doctor of a dental clinic or the like can transmit information such as a claim from the information processor 102 set up in a treatment room, to the information processor 103 at a call center installed on the communication network NW. When the information processor 103 at the call center acquires information on a failure or the like from the dental treatment apparatus 101 or the information processor 102 in the dental clinic, via the communication network NW, the call center can take appropriate measures against the failure.

The information on temperature of the instrument 110 may be stored and managed in the cloud server 105 on the communication network NW. As described above, the information on temperature of the instrument 110 can be managed in various locations any time.

As described above, the medical treatment instrument temperature information management device 50 according to this embodiment includes: the wireless tag 10 which is disposed at the instrument 110; and the reader-writer 20 as a reading unit which reads data from the wireless tag 10. The wireless tag 10 includes: the temperature sensor 13; and the IC chip 11 which includes the storage part 11b. The wireless tag 10 makes the storage part 11b store therein temperature information on temperature of the instrument 110, based on a value detected by the temperature sensor 13.

In this embodiment as described above, the temperature information on temperature of the instrument 110 is stored in the storage part 11b of the wireless tag 10, based on the value detected by the temperature sensor 13 of the wireless tag 10 disposed at the instrument 110. Thus it can be prevented that, for example, even when a sterilization treatment for heating and sterilizing the instrument 110 has not yet been actually performed, erroneous information showing that the sterilization treatment has already been performed, though in fact it has not been done, is stored in the storage part 11b of the wireless tag 10.

The temperature information on temperature of each of the instruments 110 can be therefore managed with reliability.

In this embodiment, when a value detected by the temperature sensor 13 has reached a prescribed temperature range, the storage part 11b of the wireless tag 10 disposed at the instrument 110 can store therein such necessary temperature information. Thus it can be prevented that, even when the detected value has not yet reached the prescribed temperature range, erroneous information on the temperature is stored in the storage part 11b.

In this embodiment, when a sterilization treatment in which the instrument 110 is heated for sterilization, necessary temperature information can be stored in the storage part 11b of the wireless tag 10 disposed at the instrument 110. Thus it can be prevented that, even if the sterilization treatment has not yet been actually performed to the instrument 110, erroneous information indicating that the sterilization treatment has already been performed is stored in the storage part 11b of the wireless tag 10 at the instrument 110. This makes it possible to prevent that the instrument 110 to which necessary sterilization treatment has not yet been subjected is improperly used.

In addition, in this embodiment, when the temperature sensor 13 detects that the instrument 110 has reached a temperature range equal to or higher than a sterilization temperature, information indicating that the sterilization treatment has been performed is automatically stored in the storage part 11b of the wireless tag 10. Therefore, unlike in the conventional technology, there is no need for a user such as a doctor of a dental clinic or the like to take the trouble of bringing the instrument 110 close to the reader-writer 20 so as to make the reader-writer 20 read the wireless tag 10 before and after the sterilization treatment. Failure in storing necessary temperature information in the storage part 11b of the wireless tag 10 can also be prevented.

In this embodiment, the temperature information includes the sterilization information indicating the number of times of sterilization which is the number of times sterilization treatments have been performed to the instrument 110. This makes it possible to know the number of times of sterilization having been performed to the instrument 110 whenever necessary. How much number of times sterilization has been performed to each of the instruments 110 can be thus checked. Maintenance of each of the instruments 110 can also be managed.

In this embodiment, the temperature information includes the sterilization information indicating a date and time when a sterilization treatment is performed to the instrument 110. This makes it possible to know the date and time when the sterilization has been performed to the instrument 110. The latest date and time of the sterilization of the instrument 110 can be thereby checked. Maintenance of each of the instruments 110 can also be managed.

In this embodiment, when the instrument 110 has a temperature within a range too high or too low to be stored in good condition within which a temperature of a surrounding environment of the instrument 110 during transportation after shipment or during storage is not appropriate, the storage part 11b of the wireless tag 10 can store therein information indicating that the temperature is not suitable for storing the instrument 110. Similarly, when, for example, a motor or any other component of the instrument 110 generates abnormal heat, the storage part 11b of the wireless tag 10 stores therein such temperature information. Thus, when performance of the instrument 110 is decreased or a periodic maintenance thereof is carried out, for example, a manufacture reads the temperature information stored in the storage part 11b of the wireless tag 10 and can make use of the information for finding cause of a failure or the like. This makes it possible to smoothly fix or maintain the instrument 110.

In this embodiment, the wireless tag 10 has the battery 14 built therein and can thereby obtain a value detected by the temperature sensor 13 any time when necessary, with power supplied by the battery 14. Thus, wherever the instrument 110 is placed, the wireless tag 10 can make the storage part 11b store therein temperature information on temperature of the instrument 110.

In this embodiment, the instrument 110 is held in the hanger 112 of the dental treatment apparatus 101 when the instrument 110 is used for dental treatment. This allows that the reader-writer 20 as a reading unit in which at least the antenna 22 is disposed on the hanger 112 can read the wireless tag 10 disposed at the instrument 110. A user such as a doctor of a dental clinic or the like can thereby know temperature information on temperature of the instrument 110. Thus, for example, erroneous usage of the instrument 110 which has not yet been subjected to necessary sterilization treatment can be further prevented.

In this embodiment, the temperature information on temperature of the instrument 110 can be checked up at the information processors 103, 104, and the cloud server 105 on the communication network NW. Also, the temperature information on temperature of the instrument 110 can be stored in the information processors 103, 104, and the cloud server 105. Thus, various types of information on maintenance, failure, advice, or the like regarding the instrument 110 can be obtained from the information processors 103, 104, and the cloud server 105.

The present invention has been explained as above with reference to the embodiment thereof. The present invention is not, however, limited to the configuration explained in the embodiment. The configurations described in the embodiment can be changed where appropriate, within a scope not departing from the gist of the present invention, including appropriate combination or selection of the configurations described in the embodiment. Any of the configurations in the embodiment can also be added with or substituted by another configuration or can be deleted.

In the embodiment described above, for example, the reader-writer 20 reads various types of information such as the temperature information stored in the storage part 11b of the wireless tag 10. However, in a case where the various types of information is used only for checking the temperature information on temperature of the instrument 110, a reader (a reading unit) for reading purpose only may be used, instead of the reader-writer 20.

In the embodiment described above, when a value detected by the temperature sensor 13 has reached a prescribed range, such temperature information is stored in the storage part 11b of the wireless tag 10. In this case, however, the value detected by the temperature sensor 13 may be configured to be stored in the storage part 11b successively. In the above-described configuration, a temperature history along with passage of time of each of the instruments 110 can be managed.

In the embodiment described above, the built-in battery 14 supplies the wireless tag 10 with power. Another configuration is also possible in which a wireless power feeder is provided which supplies power to the wireless tag 10 without contact thereto. The wireless power feeder is structured to be attached to the sterilizer 120, the container 130, or the like. When the wireless power feeder is attached to the sterilizer 120, it is preferable that a power transmission coil is disposed inside the sterilizer 120 and also that a main body of the power feeder is installed outside and adjacent to the sterilizer 120. This is intended to make sure to supply power to the wireless tag 10 disposed at the instrument 110 which is situated inside the sterilizer 120.

In the above-described configuration, the wireless tag 10 can obtain a value detected by the temperature sensor 13 through power supply from the wireless power feeder. This makes it possible for the wireless tag 10 to have a simple and compact structure. This also allows the wireless tag 10 to make the storage part 11b store therein temperature information on temperature of the instrument 110, within a range in which the wireless tag 10 can receive power from the wireless power feeder.

The medical treatment instrument temperature information management device 50 may also be configured to include: a wireless tag which has the temperature sensor 13 which is disposed at the instrument 110 and detects a temperature or an ambient temperature of the instrument 110, and a transmission part such as an antenna which transmits temperature information based on a value detected by the temperature sensor 13; and a storage part which is disposed outside the wireless tag. In this structure, the wireless tag: transmits the temperature information based on the value detected by the temperature sensor 13; and makes the externally-provided storage part store therein the information. That is, such a structure is also possible in which: the information obtained from the temperature sensor 13 is wirelessly transmitted and is stored from the wireless tag into, for example, a storage part of the cloud server 105. The structure described above makes it possible to prevent that, for example, even when a sterilization treatment for heating and sterilizing the instrument 110 has not yet been actually performed, erroneous information showing that the sterilization treatment has already been performed is stored in the externally-provided storage part.

In the embodiment described above, the medical treatment instrument temperature information management device 50 is configured to manage temperature information on temperature of the dental instrument 110. The present invention is not, however, limited to this. The medical treatment instrument temperature information management device 50 may also be configured to manage temperature information on, for example, temperature of various types of medical treatment instruments such as a medical surgical instrument.

DESCRIPTION OF REFERENCE NUMERALS

10 wireless tag
11 IC chip
11a control part
11b storage part
12 antenna
13 temperature sensor
14 battery
20 reader-writer (reading unit)
21 reader-writer main body
22 antenna
50 medical treatment instrument temperature information management device
100 dental treatment service system
101 dental treatment apparatus
102-104 information processor
105 cloud server
110 dental instrument (medical treatment instrument)
111 main unit
112 hanger
113 holder
120 sterilizer
130 container
NW communication network

The invention claimed is:

1. A medical treatment instrument temperature information management device which manages temperature information on temperature of a medical treatment instrument, the medical treatment instrument temperature information management device, comprising:
a wireless tag that is disposed at the medical treatment instrument and that includes a temperature sensor which detects a temperature of the medical treatment instrument or an ambient temperature thereof,
a storage part; and
a reading unit that is configured to read data from the wireless tag; and
a wireless power feeder which supplies power to the wireless tag without contact thereto,
wherein the medical treatment instrument is a dental instrument,
wherein the wireless power feeder is attached to a sterilizer or a container, and when the medical treatment instrument is placed at the sterilizer or the container, the wireless power feeder is provided within a range in which the wireless tag receives power from the wireless power feeder,
wherein, when attached to the sterilizer, the wireless feeder includes a power transmission coil is disposed inside the sterilizer and a main body of the power feeder installed outside the sterilizer, and
wherein the wireless tag is configured to make the storage part store therein the temperature information, based on a value detected by the temperature sensor.

2. The medical treatment instrument temperature information management device according to claim 1,
wherein the wireless tag is configured to make the storage part store therein the temperature information, responsive to the value detected by the temperature sensor reaching a prescribed temperature range.

3. The medical treatment instrument temperature information management device according to claim 2,
wherein the prescribed temperature range is a temperature range equal to or higher than a sterilization temperature in a sterilization treatment to the medical treatment instrument.

4. The medical treatment instrument temperature information management device according to claim 3,
wherein the temperature information includes sterilization information indicating the number of times of sterilization which is the number of times sterilization treatments have been performed to the medical treatment instrument.

5. The medical treatment instrument temperature information management device according to claim 4,
wherein the temperature information includes additional sterilization information indicating a sterilization date and time which is a date and time when a sterilization treatment has been performed to the medical treatment instrument.

6. The medical treatment instrument temperature information management device according to claim 2,
wherein the prescribed temperature range is a temperature range within which a temperature is not suitable for storing the medical treatment instrument.

7. The medical treatment instrument temperature information management device according to claim 1,
wherein the value detected by the temperature sensor is stored successively in the storage part.

8. The medical treatment instrument temperature information management device according to claim 1,
wherein at least an antenna of the reading unit is disposed on a hanger of the dental treatment apparatus, the hanger being used for holding the dental instrument.

9. The medical treatment instrument temperature information management device according to claim 1,
wherein the reading unit is connected to a communication network and is configured to communicate the temperature information with an information processor connected to the communication network.

10. A medical treatment instrument temperature information management device which manages temperature information on temperature of a medical treatment instrument, the medical treatment instrument temperature information management device, comprising:
a wireless tag that is disposed at the medical treatment instrument and that includes a temperature sensor which detects a temperature of the medical treatment instrument or an ambient temperature thereof, a transmission part which is configured to transmit the temperature information, based on a value detected by the temperature sensor;
a storage part that is disposed outside the wireless tag; and
a wireless power feeder which supplies power to the wireless tag without contact thereto,
wherein the medical treatment instrument is a dental instrument,
wherein the wireless power feeder is attached to a sterilizer or a container, and when the medical treatment instrument is placed at the sterilizer or the container, the wireless power feeder is provided within a range in which the wireless tag receives power from the wireless power feeder, wherein, when attached to the sterilizer, the wireless feeder includes a power transmission coil is disposed inside the sterilizer and a main body of the power feeder installed outside the sterilizer, and wherein the wireless tag is configured to transmit the temperature information and make the storage part store therein the transmitted temperature information, based on the value detected by the temperature sensor.

11. The medical treatment instrument temperature information management device according to claim 10, wherein the wireless tag is configured to make the storage part store therein the temperature information, when the value detected by the temperature sensor reaches a prescribed temperature range.

12. The medical treatment instrument temperature information management device according to claim 11, wherein the prescribed temperature range is a temperature range equal to or higher than a sterilization temperature in a sterilization treatment to the medical treatment instrument.

13. The medical treatment instrument temperature information management device according to claim 12, wherein the temperature information includes sterilization information indicating the number of times of sterilization which is the number of times sterilization treatments have been performed to the medical treatment instrument.

14. The medical treatment instrument temperature information management device according to claim 11, wherein the prescribed temperature range is a temperature range within which a temperature is not suitable for storing the medical treatment instrument.

15. The medical treatment instrument temperature information management device according to claim 10, wherein the value detected by the temperature sensor is stored successively in the storage part.

16. The medical treatment instrument temperature information management device according to claim 10, wherein at least an antenna of the reading unit is disposed on a hanger of the dental treatment apparatus, the hanger being used for holding the dental instrument.

17. The medical treatment instrument temperature information management device according to claim 10, wherein the reading unit is connected to a communication network and is configured to communicate the temperature information with an information processor connected to the communication network.

\* \* \* \* \*